United States Patent
Koster et al.

(12)

(10) Patent No.: US 6,872,865 B1
(45) Date of Patent: Mar. 29, 2005

(54) SELECTIVE DISPROPORTIONATION CATALYST AND PROCESS

(75) Inventors: Susan C. Koster, South Elgin, IL (US); Jennifer S. Holmgren, Bloomingdale, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/479,302

(22) Filed: Jan. 6, 2000

(51) Int. Cl.[7] .............................. C07C 5/52; B01J 29/06
(52) U.S. Cl. ..................... 585/475; 585/470; 502/60; 502/64; 502/69; 502/70; 502/73; 208/46
(58) Field of Search ........................... 585/470, 475; 208/46; 502/60, 61, 64, 69, 70, 73

(56) References Cited

U.S. PATENT DOCUMENTS

| | | | |
|---|---|---|---|
| 4,097,543 A | 6/1978 | Haag et al. ............ 260/672 T |
| 4,203,869 A | 5/1980 | Rollmann ................ 252/455 Z |
| 4,861,739 A | 8/1989 | Pellet et al. ................ 502/64 |
| 5,972,205 A | * 10/1999 | Tsang et al. ........... 208/120.01 |
| 5,993,642 A | * 11/1999 | Mohr et al. .................... 208/46 |
| 5,998,686 A | * 12/1999 | Clem et al. .................. 585/415 |
| 6,150,293 A | * 11/2000 | Verduijn et al. .............. 502/67 |

* cited by examiner

*Primary Examiner*—Walter D. Griffin
(74) *Attorney, Agent, or Firm*—John G. Tolomei; Frank S. Molinaro; Thomas K. McBride, Jr.

(57) ABSTRACT

An improved catalytic composite and process are disclosed for the selective disproportionation of toluene. The process uses a layered composite comprising a catalytically active core which comprises a zeolitic aluminosilicate having a $SiO_2:Al_2O_3$ ratio of 8 to 50 and a relatively inactive protective mantle which preferably comprises boralite. Optionally, the composite is selectively precoked prior to toluene disproportionation. The composite and process provide improved selectivity for the production of paraxylene.

11 Claims, 4 Drawing Sheets

SELECTIVE DISPROPORTIONATION CATALYST AND PROCESS

BACKGROUND OF THE INVENTION AND RELATED ART

This invention relates to processes for the conversion of aromatic hydrocarbons, and is more specifically an improved process for disproportionation and/or transalkylation of aromatic hydrocarbons to obtain xylenes.

Xylene isomers are produced in large volumes from petroleum as feedstocks for a variety of important industrial chemicals. The most important: of the xylene isomers is paraxylene, the principal feedstock for polyester which continues to enjoy a high growth rate from large base demand. Orthoxylene is used to produce phthalic anhydride, which has high-volume but mature markets. Metaxylene is used in lesser but growing volumes for such products as plasticizers, azo dyes and wood preservers. Ethylbenzene generally is present in xylene mixtures and is occasionally recovered for styrene production, but usually is considered a less-desirable component of $C_8$ aromatics.

Among the aromatic hydrocarbons, the overall importance of the xylenes rivals that of benzene as a feedstock for industrial chemicals. Neither the xylenes nor benzene are produced from petroleum by the reforming of naphtha in sufficient volume to meet demand, and conversion of other hydrocarbons is necessary to increase the yield of xylenes and benzene. Most commonly, toluene is dealkylated to produce benzene or disproportionated to yield benzene and $C_8$ aromatics from which the individual xylene isomers are recovered. More recently, processes have been introduced to disproportionate toluene selectively to obtain higher-than-equilibrium yields of paraxylene.

A current objective of many aromatics complexes is to increase the yield of xylenes and to deemphasize benzene production. Demand is growing faster for xylene derivatives than for benzene derivatives. Refinery modifications are being effected to reduce the benzene content of gasoline in industrialized countries, which will increase the supply of benzene available to meet demand. Benzene produced from disproportionation processes often is not sufficiently pure to be competitive in the market. A higher yield of xylenes at the expense of benzene thus is a favorable objective, and processes to transalkylate $C_9$ aromatics along with toluene have been commercialized to obtain high xylene yields.

U.S. Pat. No. 4,097,543 (Haag et al.) teaches toluene disproportionation for the selective production of paraxylene using a zeolite which has undergone controlled precoking. The zeolite may be ion-exchanged with a variety of elements from Group IB to VIII, and composited with a variety of clays and other porous matrix materials.

U.S. Pat. No. 4,203,869 discloses a zeolite having an aluminum-free outer shell of $SiO_2$ which has the same crystal structure as the zeolite. The zeolite is made by a two-stage method of initiating crystallization of the zeolite, then altering the crystallization medium to eliminate the aluminum moiety.

U.S. Pat. No. 4,861,739 discloses a multiphase, multi-compositional composite, at least one phase of which is a "QAPSO" non-zeolitic molecular sieve (NZMS) comprising phosphorus, aluminum and another element Q. Much of the benefits of NZMSs as catalysts are achieved in the outer portion of a particle, and secondary reactions in the core of a particle are avoided with this invention.

U.S. Pat. No. 4,482,774 (W. T. Koetsier) presents hydrocarbon conversion processes, including toluene disproportionation, which are performed using a catalyst having a core of silica with an overlying modified-silica zeolite, having substantially the same crystalline structures. The core is described as having only a few acid sites and little catalytic activity, and preferably having a ratio of silicon to modifying elements above 500. The core may have an MFI structure. The modified silica shell of this catalyst may have many compositions including a specified borosilicate and gallosilicate.

Workers in the field of aromatics disproportionation continue to seek processes and catalysts having exceptionally high selectivity for paraxylene from toluene combined with favorable activity and stability.

SUMMARY OF THE INVENTION

It is an object of the present invention to provide an improved catalyst and process for the disproportionation of aromatic hydrocarbons to yield desirable alkylaromatic isomers. A specific objective is to obtain a high yield of paraxylene by disproportionation of toluene.

This invention is based on the discovery that undesirable side reactions in the disproportionation of toluene are suppressed using a layered composite having a zeolitic aluminosilicate core of MFI isotype with a boralite mantle. The present invention therefore is directed to a layered crystalline composite of a single zeolitic isotype comprising a core which comprises a zeolitic aluminosilicate selected from EUO, MFI, MEL, MFS, MTW, TON and MCM-22, and a mantle comprising a crystalline metallosilicate containing a framework metal capable of forming stable +3 ions, preferably selected from one or more of B. In, Ga and Fe. The catalytically active core zeolite preferably is of the MFI isotype, commonly referred to as ZSM-5. The crystalline metallosilicate of the protective mantle preferably is boralite. Optimally, the composite has a substantial absence of phosphorus. A preferred composite consists essentially of a core of MFI zeolitic aluminosilicate, a mantle of boralite, and an aluminum phosphate binder.

In another aspect, the invention comprises a process for the synthesis of a layered composite of a single zeolitic isotype by crystal growth of a mantle phase comprising a crystalline metallosilicate in the presence of a core which comprises a 10-12 ring zeolitic aluminosilicate selected from MFI, MEL and MTW and TON zeolites.

The invention also comprises hydrocarbon conversion processes using the composite of the invention, and particularly a process for the disproportionation of a toluene feedstock using the present composite to obtain a product comprising paraxylene. Preferably the product contains paraxylene in excess of its equilibrium concentration at the chosen disproportionation conditions. The composite preferably is subjected to a precoking step prior to its use for disproportionation/transalkylation in order to deposit a controlled concentration of carbon on the composite and increase its selectivity to paraxylene in the product. A process combination optionally comprises a xylene-separation zone using crystallization and/or adsorptive separation.

These as well as other objects and embodiments will become apparent from the detailed description of the invention.

DESCRIPTION OF THE PREFERRED EMBODIMENTS

The crystalline composite of the present invention comprises a zeolitic aluminosilicate in integral lattice association, or epitaxial alignment, with a crystalline metallosilicate comprising one or more elements capable of forming stable +3 ions, preferably framework B, In, Ga, or Fe. The zeolitic aluminosilicate comprises the active core, or substrate, while the metallosilicate comprises the mantle, outer layer or shell, of the composite. The core and mantle are integrally bonded to each other by the growth of one crystal phase from another such that the composite is of a common crystal structure or zeolitic isotype. The phases of the composite thus are in integral lattice association with each other through, it is believed, direct chemical linkages rather than being simple physical mixtures or joined by a third component. The composite nevertheless has a heterogeneous chemical composition, i.e., the phases of the composite are crystallographically indistinct with compositional heterogeneity.

The composite of the present invention thus comprises a layered crystalline metallosilicate wherein the layers are contiguous, compositionally heterogeneous and of a single zeolitic isotype and comprise a catalytically active core comprising a zeolitic aluminosilicate and a mantle comprising a crystalline metallosilicate which comprises a framework metal capable of forming stable +3 ions preferably selected from one or more of the group consisting of boron, indium, gallium and iron. Specific examples of preferred zeolitic isotypes as designated in the *Atlas of Zeolite Structure Types* of the *Structure Commission of the International Zeolite Association*] are MFI, MEL, EUO, MFS, MTW, TON, and MCM-22. MFI-type zeolites, commonly designated ZSM-5, are generally optimal. The preferred core material comprises a zeolitic aluminosilicate having an $Si:Al_2$ ratio greater than about 10, preferably greater than 20, and a pore diameter [referring to crystallographic free diameter as represented in the *Atlas of Zeolite Structure Types*] of about 5 to 8 Angstroms (Å). Preferably the $SiO_2:Al_2O_3$ ratio of the core is less than 45 and may range from 20–40. The preferred framework metal of the mantle consists essentially of boron, and the mantle thus preferably consists essentially of boralite. Optimally, the composite has the substantial absence of framework phosphorus.

The layered composite has advantages in selectivity, activity and/or stability in hydrocarbon conversion over the individual components of the composite. This differential in performance relates to the relative catalytic, absorbency, and other properties of the phases of the composite and the featuring of such properties through the position and interaction of the phases in the composite. In the present composite, it is believed that the catalytic activity of the composite is primarily associated with the core while the mantle possesses properties which enhance the selectivity of the reaction, as by providing a non-reactive but porous overcoat through which reactants and products may pass without degradation. The mantle can thus protect the feed or product molecules from reactions which may be promoted by the surface of the active core material rather than in the pores of the core. Reactions in pores are impacted by the shape and size of the pores and thus can differ in rate or kind from reactions promoted by an active outer surface of the core material.

In the subject invention the mantle thus performs a protective role and the core provides the desired catalytic activity of the overall composite.

The phases of the composite are characterized according to known zeolitic compositions, since the phases are prepared based on components and methods of manufacture which, according to the art, would generate such zeolitic compositions. However, it is believed that phases exist within the composite which differ from the compositions of either the core or the mantle. The significant difference resides in the chemical composition of the interface between phases. There is a propensity for redissolving a part of the core by the components of the mantle during the deposition of one phase onto another, thus causing a chemical change in the portion of the interface which nominally belongs to the core. Further, there is a capacity for ion exchange through ionic mobility of contiguous layers. Such alterations are relatively small, however, and may not be detectable by usual analytical methods such as nuclear magnetic resonance (NMR). In any event the crystal structure and zeolitic isotype remain essentially constant throughout the zeolitic composite.

The relationship of the phases through a common crystal structure is demonstrated through X-ray powder diffraction or other evidence of crystallinity. The X-ray powder diffraction patterns for the multiple phases of the composite is the same in essential details. The patterns may differ due to the sizes of different framework cations, but the differences are slight enough that one would regard the different phases to be framework-compatible in essential crystallographic terms. Determination and characterization of crystallinity are not limited to X-ray diffraction as a technique, however, as other procedures can be employed to demonstrate the existence of a crystal structure. Such techniques include, either alone or in combination, electron diffraction analysis, molecular adsorption data, and adsorption isotherm characterizations.

Effective crystalline composites can have relative proportions of core and mantle within a wide range of values. The mantle layer should be at least one unit cell in width in order to be effective, while the core should be sufficient to maintain its chemical integrity during preparation of the composite. Preferably the amount of the mantle ranges from about 1 mass-% to about 90 mass-%, with the core amounting to from about 10 mass-% to about 99 mass-%, of the composite. More preferably, the mantle comprises from about 2 mass-% to about 80 mass-% of the composite. The thickness of the mantle optimally is less than that of the core, measured through the center of a particle of the composite. Preferably the composite is a particle having an average cross-section of from about 0.2 to 100, and more preferably about 1 to 50, microns.

It is within the scope of the invention that the core of the composite is circumscribed by more than one mantle. In this embodiment, an inner mantle comprises part of the core with respect to an outer mantle. Each mantle and core in contact with each other is of a different chemical composition, although of the same crystal structure and isotype. In another embodiment, the core is an aggregate or agglomerate of particles having one or more of a variety of shapes and surrounded by the mantle.

The preferred zeolitic aluminosilicates of the composite core are prepared by methods known in the art. The zeolites generally are prepared by crystallizing an aqueous mixture containing reactive sources of silica and alumina and a templating agent, and usually an alkyl ammonium compound or its precursor, at a temperature of from about 25° to 300° C. for a period of time sufficient to effect crystallization. MFI zeolite, often designated ZSM-5, and its preparation are described in, e.g., U.S. Pat. No. 3,702,886; MEL or ZSM-11 in U.S. Pat. No. 3,709,979; MTW or ZSM-12 in U.S. Pat. No. 3,832,449; and TON or ZSM-22 in EP-+A-170,003 or U.S. Pat. No. 4,046,859; all of which are incorporated herein by reference. The preferred zeolitic aluminosilicate is an MFI isotype generally characterized by an empirical chemical composition on an anhydrous basis expressed by the formula:

$$0.9\pm0.2X_{2/n}O:Al_2O_3:ySiO_2$$

where X is a cation of valence n and y is between about 8 and 2000. However, it is preferred to employ a material having a $SiO_2:Al_2O_3$ ratio less than about 80 in the subject invention. More preferably this ratio is less than 40, with a range of 20–40 or 25–40 providing suitable acidity for the desired catalytic activity.

In one embodiment of synthesizing the composite, the core or substrate is present as a preformed zeolitic aluminosilicate, i.e., a fully formed crystalline structure. The template may or may not be essentially removed, and the aluminosilicate then is contacted with the components which are used to generate the mantle.

The mantle is formed typically by crystallizing an aqueous mixture at controlled pH comprising a metal compound, an oxide of silicon and an organic template compound. The metal, comprising one or more selected from the group consisting of boron, indium, gallium and iron, may be introduced into the reaction system in any compound and manner which permits the formation in situ of a reactive form of the metal; i.e., in a compound which is reactive to form a framework oxide of the metal. Such metal compounds include but are not limited to oxides, hydroxides, alkoxides, nitrates, sulfates, halides, carboxylates and mixtures thereof. A crystalline metallosilicate is formed characterized by an empirical chemical composition on an anhydrous basis expressed by the formula:

$$0.9\pm0.2X_{2/n}O:M_2O_y:zSiO_2$$

where X is a cation of valence n, M is a metal of valence y selected from one or more of the group consisting of boron, indium, gallium and iron and z is between about 4 and 500.

Preferably the metal is boron introduced as boric acid or an alkoxide. In this preferred embodiment, the mantle of the composite is boralite. Optimally, the framework metal of the mantle consists essentially of boron. The boralite mantle suitably is effected by the hydrothermal crystallization of reactive gel precursors to the crystal structure in the presence of the core or substrate. The reaction mixture generally contains an oxide of silicon, an oxide of boron, an organic templating (structure-directing) agent, and optionally an alkali or alkaline earth metal in combination with the core material.

By regulating the ratio of silicon to boron in the reaction mixture, the molar ratio of $SiO_2/B_2O_3$ in the boralite may be varied between about 4 and 600 or more. When aluminum in the crystal structure is minimized, the $SiO_2/Al_2O_3$ ratio can easily exceed 1000, as limited by the availability of aluminum-free raw materials. Preferably the crystalline metallosilicate is boralite characterized by an empirical chemical composition on an anhydrous basis expressed by the formula:

$$0.9\pm0.2X_{2/n}O:B_2O_3:ySiO_2$$

where X is a cation of valence n and y is between about 4 and 600.

The source of silicon may be one or more of silica, either as a silica sol or fumed silica, a reactive solid amorphous precipitated silica, silica gel, alkoxides of silicon, silica-containing clays, silicic acid, or alkali metal silicate.

The preferred boron can be introduced into the reaction mixture in any form which permits the formation of framework boron in the mantle. Suitable oxides of boron include boric acid ($H_3BO_3$), $B_2O_3$ and $B_4O_7$.

The organic templating agent preferably is a compound of a Group VA (IUPAG 15) element, preferably of nitrogen or phosphorus, and most preferably of nitrogen. Mono-, di-, tri- and tetra-amines are favored, either alone or in combination with a quaternary ammonium or other compound. Di- and tri-ethyl and -propyl amines are particularly favored, especially tri-n-propyl and tri-isopropyl amines when forming the preferred mantles of the present invention.

Hydrothermal crystallization to form the mantle of the present invention is carried out by reacting an aqueous mixture containing the aluminosilicate solids and reactive sources of silica and metal and a templating agent at a temperature of between about 25° and 300° C. for an effective crystallization time which typically ranges between about one hour and four weeks. The favored boralite is formed at a temperature of between about 100° and 250° C. over a period of between about four hours and two weeks. It generally is preferable to utilize ammonium salts to maintain the integrity of the core or substrate and avoid its decomposition resulting from excessive concentrations of caustic, furnishing a system pH generally within the range of about 9 to about 13.5. The product is recovered by any suitable method such as filtration or centrifugation. The recovered product typically is washed with water and dried in air.

The resulting as-synthesized composite generally contains within its pores at least a portion of any templating agent, usually an organic moiety, employed in its formation. Part of this agent commonly is present as a charge-balancing cation. Some or all of the organic moiety, however, may be occluded organic species which is too large to move freely through the pore system of the product. This species must be removed by activation or calcination at a temperature between about 250° and 700° C., and more typically below about 600° C. to avoid damage to the crystal structure, for a period of from about 1 to 15 hours.

Further details of the characterization and preparation of an embodiment of boralite are disclosed in U.S. Pat. No. 4,269,813, incorporated herein by reference.

The original cations of the composite can be replaced in accordance with techniques known in the art by ion exchange with other cations either in part or substantially completely. Preferred replacing cations include those of the metals, particularly of Groups IA (IUPAC 1), IIA (2) and VIII (8-10); hydrogen, ammonium and tetraalkylammonium.

A catalytic composite may be formed from particles of the composite as such or the composite can comprise a binding medium to bond the particles together into desired shapes. A refractory binder or matrix usually is utilized to facilitate fabrication, provide strength and reduce fabrication costs of the catalytic composite. The amount of crystalline composite present in a bound catalytic composite can vary considerably but usually is present in an amount from about 30 to 90 mass percent and preferably from about 50 to 80 mass percent. The binder should be uniform in composition and relatively refractory to the conditions used in the process. Suitable binders include inorganic oxides such as one or more of alumina, magnesia, zirconia, chromia, titania, boria, thoria, zinc oxide, phosphorus oxide and silica. Preferred binders comprise one or more of alumina, silica and phosphorus oxide.

A preferred binder or matrix component is a phosphorus-containing alumina (hereinafter referred to as aluminum phosphate) component. The phosphorus may be composited with the alumina in any acceptable manner known in the art. The zeolite and aluminum phosphate binder are mixed and formed into particles by means well known in the art such as gellation, pilling, nodulizing, marumerizing, spray drying, extrusion or any combination of these techniques; the form or preparation of particles of the catalytic composite is not a critical aspect of the invention. A preferred method of preparing the zeolite/aluminum phosphate support involves adding the zeolite either to an alumina sol or a phosphorus compound, forming a mixture of the alumina sol/zeolite/phosphorus compound into particles by employing an oil-drop method as described hereinbelow and calcining the spherical particles.

The preferred oil-drop method of preparing the aluminum phosphates is described in U.S. Pat. No. 4,629,717 which is incorporated by reference. The technique described in the '717 patent involves the gellation of a hydrosol of alumina which contains a phosphorus compound using the well-known oil-drop method. Generally this technique involves preparing a hydrosol by digesting aluminum in aqueous hydrochloric acid at reflux temperatures of about 80° to 105° C. The ratio of aluminum to chloride in the sol ranges from about 0.7:1 to 1.5:1 mass ratio. A phosphorus compound is now added to the sol. Preferred phosphorus compounds are phosphoric acid, phosphorous acid and ammonium phosphate. The relative amount of phosphorus and aluminum expressed in molar ratios ranges from about 10:1 to 1:100, respectively, on an elemental basis. The zeolite is added to the aluminum phosphate hydrosol and the mixture is gelled. One method of gelling this mixture involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The combined mixture preferably is dispersed into the oil bath in the form of droplets from a nozzle, orifice or rotating disk. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours Alternatively, the particles may be formed by spray-drying of the mixture at a temperature of from about 425° to 760° C. In any event, conditions and equipment should be selected to obtain small spherical particles; the particles preferably should have an average diameter of less than about 1.0 mm, more preferably from about 0.2 to 0.8 mm, and optimally from about 0.3 to 0.8 mm.

The amount of phosphorus-containing alumina component present (as the oxide) in the preferred composite can range from about 10 to 70 mass percent and preferably from about 20 to 50 mass percent. The aluminum phosphate binder/matrix optionally may contain lesser proportions of other inorganic oxides including, but not limited to, magnesia, beryllia, boria, silica, germania, tin oxide, zinc oxide, titania, zirconia, vanadia, iron oxide, chromia, cobalt oxide and the like which can be added to the hydrosol prior to dropping.

The degree of crystallinity of the aluminum phosphate binder or matrix can be controlled by varying the proportion of the phosphorus component. Material that is not in an amorphous phase generally is present as gamma-alumina; as the phosphorus content is decreased, the degree of crystallinity therefore is increased. The average bulk density of the spheres also varies with the phosphorus content, as a higher proportion of phosphorus decreases the average bulk density. Surface area also is controlled by phosphorus content: gamma-alumina oil-dropped spherical particles typically have surface areas up to about 250 $m^2/g$, while spheroidal particles of aluminum phosphate may have surface areas of up to about 450 $m^2/g$. Al/P atomic ratios of the binder generally range from respectively about 1:10 to 100:1, and more typically from about 1:5 to 20:1. Preferably the Al/P atomic ratio of the binder is between about 2:1 and 10:1, and more preferably between about 3:1 and about 5:1.

It is within the scope of the invention that the composite contains a metal component, preferably selected from components of the group consisting of gallium, rhenium and bismuth. Preferably, however, the composite consists essentially of the layered crystalline composite and an aluminum phosphate binder.

The present composite is useful for a variety of processes for the conversion of hydrocarbons to obtain a converted product. The composite preferably is utilized in combination with at least one inorganic-oxide matrix and one or more metals as described herein. A hydrocarbon feedstock is converted at hydrocarbon-conversion conditions including a pressure of about 100 kpa to 20 MPa, temperatures of about 50° to 600° C., liquid hourly space velocities of from about 0.1 to 100 $hr^{-1}$, and, if hydrogen is present, hydrogen-to-hydrocarbon molar ratios of from about 0.1 to 80. Hydrocarbon-conversion processes which could advantageously employ catalytic compositions containing the sieves of the invention include isomerization, reforming, dehydrocyclization, dehydrogenation, disproportionation, transalkylation, dealkylation, alkylation, polymerization, hydrocracking and catalytic cracking.

Composites of the invention used in reforming processes preferably contain a hydrogenation promoter such as a platinum-group metal and optionally one or more modifiers such as rhenium and Group IVA (IUPAC 14) metals on an inorganic-oxide support. Hydrocarbon feedstocks, preferably naphtha, contact the catalyst at pressures of between 100 kPa and 4 MPa, temperatures of about 350 to 600° C., liquid hourly space velocities (LHSV) from 0.2 to 20 $hr^{-1}$, and hydrogen-to-hydrocarbon molar ratios of from about 0.1 to 10. Dehydrocyclization of naphthas and other paraffin-containing stocks is carried out over a similar catalyst, preferably nonacidic through incorporation of an alkali or alkaline earth metal, at similar conditions with operating pressure no higher than about 15 MPa. Products of reforming and dehydrocyclization generally have an increased concentration of aromatics relative to the feedstocks.

Isomerization of light hydrocarbons is advantageously effected using composites within the scope of those described for use in reforming processes. The light hydrocarbon feedstock contacts the catalyst at pressures of between 100 kPa and 7 MPa, temperatures of about 50° to 300° C., LHSV from 0.2 to 5 hr$^{-1}$, and hydrogen-to-hydrocarbon molar ratios of from about 0.1 to 5. Isomerization of olefins such as butenes, pentenes and higher olefins is effected over a catalyst which preferably does not contain a substantial hydrogenation component, in order to avoid olefin hydrogenation, at somewhat higher temperatures of 200° to 600° C. and higher space velocities of 0.5 to 100 hr$^{-1}$. Usually isomerization yields a product having a greater concentration of branched hydrocarbons.

Heavier paraffins, waxy distillates and raffinates are isomerized to increase the branching of the hydrocarbons using broadly the same composites as described for reforming. Operating conditions include pressures of between about 2 and 15 MPa, temperatures of about 200° to 450° C., LHSV from $O_2$ to 110 hr$^{-1}$, and hydrogen-to-hydrocarbon molar ratios of from about 0.5 to 10.

Composites of the invention used in hydrocracking processes preferably contain a hydrogenation promoter such as one or more of Group VIII (IUPAC 8-10) and Group VIB (IUPAC 6) metals and an inorganic-oxide matrix. A variety of feedstocks including atmospheric and vacuum distillates, cycle stocks and residues are cracked to yield lighter products at pressures of between 3 and 20 MPa, temperatures of about 200 to 450° C., LHSV from 0.1 to 10 hr$^{-1}$, and hydrogen-to-hydrocarbon molar ratios of from about 2 to 80.

Composites of the same general description as those used in hydrocracking processes are useful in hydrotreating and hydrofining. A variety of naphthas, atmospheric and vacuum distillates, cracked and cycle stocks and residues are treated to remove sulfur, nitrogen and other heteroatoms and to saturate unsaturates at pressures of between 3 and 15 MPa, temperatures of about 200° to 450° C., LHSV from 0.1 to 20 hr$^{-}$1, and hydrogen-to-hydrocarbon molar ratios of from about 2 to 20. Operating conditions vary with respect to the difficulty of heteroatom removal, usually relating to the size and aromaticity of the containing molecules, and the concentration particularly of nitrogen in the feedstock. Products meet environmental requirements, are not as corrosive or contaminating of downstream equipment, and/or effect less deactivation of catalysts in downstream-processing units relative to the feedstock.

Isomerization of alkylaromatics, particularly a $C_8$-aromatic mixture containing ethylbenzene and xylenes, is effected with the composite of the invention preferably comprising a Group VIII (IUPAC 8-10) metal. Alkylaromatic-isomerization conditions comprise a temperature preferably in the range of from about 300° to 500° C., pressure from about 1 to 10 MPa absolute, and liquid hourly space velocity of charge stock of from about 0.1 to 30 hr$^{-1}$, and preferably 0.5 to 10 hr$^{-1}$. Hydrogen, if present, is admixed with the feedstock at a hydrogen/hydrocarbon mole ratio of about 0.5:1 to about 25:1 or more.

Disproportionation is a particularly propitious use for the composite of the invention. Suitable feedstocks include single-ring aromatics, naphthalenes and light olefins. The preferred feedstock to a disproportionation process comprises substantially pure aromatic hydrocarbons derived from one or more sources. Aromatics may be produced synthetically, for example, from naphtha by catalytic reforming or by pyrolysis followed by hydrotreating to yield an aromatics-rich product. The aromatics feedstock may be derived from such The feedstock to a disproportionation process comprises substantially pure aromatic hydrocarbons derived from one or more sources. Aromatics may be produced synthetically, for example, from naphtha by catalytic reforming or by pyrolysis followed by hydrotreating to yield an aromatics-rich product. The aromatics feedstock may be derived from such product with suitable purity by extraction of aromatic hydrocarbons from a mixture of aromatic and nonaromatic hydrocarbons and fractionation of the extract. Large quantities of aromatic hydrocarbons are recovered commercially in this manner. For instance, aromatics may be recovered from a reformate through the use of a selective solvent, such as one of the sulfolane type, in a liquid—liquid extraction zone. When the severity of reforming or pyrolysis is sufficiently high, extraction may be unnecessary and fractionation may be sufficient to prepare the feedstock which should contain no more than about 10 mass-% and preferably less than about 1 mass-% nonaromatics. The recovered aromatics may then be separated into streams having the desired carbon number range by fractionation. The aromatic hydrocarbons may comprise one or more of toluene, xylene isomers, ethylbenzene, or $C_9$ and heavier aromatics. An especially preferred toluene feedstock prepared in this manner usually is fractionated to separate benzene and $C_8$ aromatics, and the degree of fractionation may be adjusted in accordance with economic factors of the disproportionation process.

The toluene feedstock, usually in admixture with toluene recycled from the products of the disproportionation reaction, is preferably admixed with free hydrogen to effect a combined feed to a disproportionation zone. If present, the hydrogen need not exceed a 20:1 molar ratio to feedstock hydrocarbons to effect satisfactory stability in the disproportionation reaction, and preferably is in the range of from about 0.5 to 10 molar ratio. The hydrogen may contain hydrocarbons, such as methane and ethane, and inerts such as nitrogen, but preferably is in a concentration of at least about 90 mole-% to avoid large hydrogen losses and unfavorable process economics. The disproportionation reaction yields a paraxylene-containing product which usually also comprises benzene, other $C_8$ aromatics, and smaller amounts of $C_9$+aromatics.

The combined feed to the disproportionation zone usually is first heated by indirect heat exchange against the effluent of the reaction zone and is then further heated in a fired heater. The resulting vaporous stream is then passed through a reaction zone which may comprise one or more individual reactors. The use of a single reaction vessel having a fixed cylindrical bed of catalyst is preferred, but other reaction configurations utilizing moving beds of catalyst or radial-flow reactors may be employed if desired. Passage of the combined feed through the reaction zone effects the production of a vaporous effluent stream comprising hydrogen and both product and unconverted feed hydrocarbons. This effluent is normally cooled by indirect heat exchange against the stream entering the reaction zone and then further cooled through the use of air or cooling water. The temperature of the effluent stream generally is lowered by heat exchange sufficiently to effect the condensation of substantially all of the feed and product hydrocarbons having six or more carbon atoms per molecule. The resultant mixed-phase stream is passed into a vapor-liquid separator wherein the two phases are separated and from which the hydrogen-rich vapor is recycled to the reaction zone. The condensate from the separator is passed into a stripping column in which substantially all $C_5$ and lighter hydrocarbons present in the effluent are concentrated into an overhead stream and removed from the process. An aromatics-rich stream which is referred to herein as the disproportionation effluent stream is recovered as net stripper bottoms.

Conditions employed in the disproportionation zone of the subject process normally include a temperature of from about 200° to 600° C., and preferably from about 350° to 575° C. The temperature required to maintain the desired degree of conversion will increase as the composite gradually loses activity during processing. Normal end-of-nun temperatures may therefore exceed start-of-run temperatures by 65° C. or more. In the transalkylation embodiment wherein toluene and $C_9$ aromatics are present in the combined feed, reaction temperatures generally are somewhat lower within the range of about 200° to 525° C.

The disproportionation zone is operated at moderately elevated pressures broadly ranging from about 100 kPa to 6 MPa absolute. A preferred pressure range is from 2 to 3.5 MPa. The disproportionation reaction can be effected over a wide range of space velocities, with higher space velocities effecting a higher ratio of paraxylene at the expense of conversion. Liquid hourly space velocities generally are the range of from about 0.2 to 10 $hr^{-1}$, with a value in the range of from 0.8 to 3 $hr^{-1}$ being preferred.

Optionally, the composite may be subjected to precoking in order to increase the proportion of paraxylene in the $C_8$ aromatics product. Precoking of the present composite effects a proportion of paraxylene in the product above equilibrium levels at disproportionation conditions, preferably at least about 80 mass-% and optimally about 90 mass-% or more of the $C_8$ aromatics. Precoking is effected on the fresh or regenerated catalytic composite prior to its use for disproportionation at precoking conditions comprising usually at one or more of a higher temperature, lower space velocity, and lower hydrogen-to-hydrocarbon ratio relative to the disproportionation conditions. Such operating conditions generally are within the ranges of those disclosed before for disproportionation, with operating temperature preferably being at least about 90° C. higher than the disproportionation temperature. Precoking time ranges from about 0.5 hours to 10 days. Precoking effects a composite carbon content of between about 5 and 40 mass-% carbon, and preferably between about 10 and 30 mass-% carbon. A coke-forming feed for precoking may comprise the feedstock as described herein, or other specific hydrocarbons or mixtures preferably comprising aromatics may be used. Further details relative to precoking are disclosed in U.S. Pat. No. 4,097,543, incorporated herein by reference.

In an alternative embodiment, the combined feed includes a heavy-aromatics stream comprising $C_9$ aromatics as a component of the combined feed to the present process. Transalkylation of toluene and $C_9$ aromatics is effected thereby within the disproportionation conditions described hereinabove The heavy-aromatics stream may be derived from the same or different known refinery and petrochemical processes as the toluene feedstock and/or may be recycled from the separation of the product from disproportionation/transalkylation. Benzene also may be present in the combined feed to disproportionation/transalkylation. However, it is preferred that the feedstock consists essentially of toluene in order to effect a high degree of paraxylene selectivity as described hereinbelow.

The disproportionation effluent stream is separated into a light recycle stream, a paraxylene-containing mixed-$C_8$-aromatics product and a heavy-aromatics stream. The paraxylene-containing product may be sent to a xylene separation zone for recovery of pure paraxylene; optionally, other xylenes and ethylbenzene also may be recovered as pure products. The paraxylene-containing stream preferably contains paraxylene in proportion to total xylenes in excess of its equilibrium concentration at disproportionation conditions, more preferably at least about 80 mass-% paraxylene, and most preferably at least about 85 mass-% paraxylene. The light recycle stream may be diverted to other uses such as to benzene and toluene recovery, but optionally a portion; is recycled to the disproportionation zone since it contains not only benzene and toluene but also amounts of nonaromatics which would remain with the benzene and reduce its commercial value. The heavy recycle stream contains substantially all of the $C_9$ and heavier aromatics and may be either withdrawn as a product of the process or partially or recycled to the reactor or to another processing unit if transalkylation is an objective of the process.

The xylene-separation zone may utilize one or more different separation techniques such as fractionation, crystallization or selective adsorption to recover pure paraxylene from the paraxylene-containing stream in the xylene-separation zone. Conventional crystallization is disclosed in U.S. Pat. No. 3,177,255, U.S. Pat. No. 3,467,724 and U.S. Pat. No. 3,662,013. Various other crystallization alternatives are discussed in U.S. Pat. No. 5,329,061, incorporated by reference. In an embodiment in which the paraxylene-containing product has a paraxylene content substantially in excess of the equilibrium concentration, recovery of pure paraxylene may be effected using only a single stage of crystallization corresponding to the higher-temperature purification stage of conventional crystallization.

An alternative separation zone comprises a bed of molecular sieves operated in accordance with the teaching of U.S. Pat. No. 3,201,491 to simulate the use of a continuously moving bed of molecular sieves. Subsequent improvements to the process are described in U.S. Pat. No. 3,696,107 and U.S. Pat. No. 3,626,020. Details on the operation of the xylene-separation zone may also be obtained from U.S. Pat. No. 4,039,599 and U.S. Pat. No. 4,184,943. The simulated cocurrent adsorptive separation process of U.S. Pat. No. 4,402,832 may be employed. The extract and raffinate streams may be handled as described in these references or as described in U.S. Pat. No. 4,381,419.

The skilled routineer will recognize variations in the process combination described above which are within the scope of the invention. For example, benzene as well as toluene may be charged to the disproportionation zone as a supplementary feedstock. The xylene-separation zone may use one or more of several known separation techniques such as adsorption, crystallization and fractionation. Orthoxylene and/or metaxylene may be recovered by one or more of such techniques as pure products from the xylene-separation zone.

EXAMPLES

The following examples are presented to demonstrate the present invention and to illustrate certain specific embodiments thereof. These examples should not be construed to limit the scope of the invention as set forth in the claims. There are many possible other variations, as those of ordinary skill in the art will recognize, which are within the spirit of the invention.

Example I

An MFI zeolitic aluminosilicate was prepared as a core of the composite of the invention as well as a control catalyst. 0.086 moles of $Na_2O$ was dissolved in 6 moles of water, followed by slow addition of 0.10 moles of $Al_2O_3$, and the resulting sodium aluminate solution was digested at 100° C. for one day. Tetrapropylammonium bromide was dissolved in 386 moles of water, and Ludox HS 40% was added slowly with 1 hour stirring. A NaOH solution was prepared with stirring to dissolve the solid, and the sodium aluminate solution was added to this dropwise with stirring. The resulting solution was added dropwise to the template/silica solution, stirring for two hours under a Hydrolph mixer, resulting in a solution pH of 13.06. The solution was digested at 150° C. for four days, and the solid was recovered by filtration and washed. The resulting MFI solid had the following molar composition:

3.65$(TPA)_2$O.2.64.$Na_2$O.$Al_2O_3$.2.94 $SiO_2$.580$H_2$O

The MFI solid was divided into a first portion and a second portion, and the first portion was washed, air dried, and calcined at a temperature of about 650° C. This MFI zeolitic aluminosilicate of the art was designated Composite X.

Example II

A mantle layer of the present composite was prepared by the following procedure. Ludox AS 40 was added to an ammonium hydroxide solution. $H_3BO_3$ was dissolved in water and added to the preceding solution, followed by dropwise addition of a 40% solution of (TPA)OH. The combined solution was stirred under a Hydolph mixer for one hour, resulting in a solution pH 13.57. A boralite gel recovered from the solution had the following composition:

5.77$(TPA)_2$O.11 $NH_3$.2.5 $B_2O_3$.100 $SiO_2$.492 $H_2$O

Two composites of the invention were prepared using the above solution and the second portion of the MFI solid prepared in Example I. The first of these was effected by combining 25% of the MFI solid with 75% of boralite gel, and the second contained 75% MFI solid and 25% gel. Each of the combinations was washed, air dried, and calcined at a temperature of about 650° C. The resulting composites of the invention were respectively designated Composites A and B.

Example III

Micro-reactor tests were carried out to determine the comparative performance of the composites described hereinabove in a disproportionation reaction. For each of composites A, B and X, toluene disproportionation was effected at a variety of conversions over a period of two hours. The ratio of paraxylene to orthoxylene in the product was measured as an indication of the selectivity of the reaction.

Figure 1:
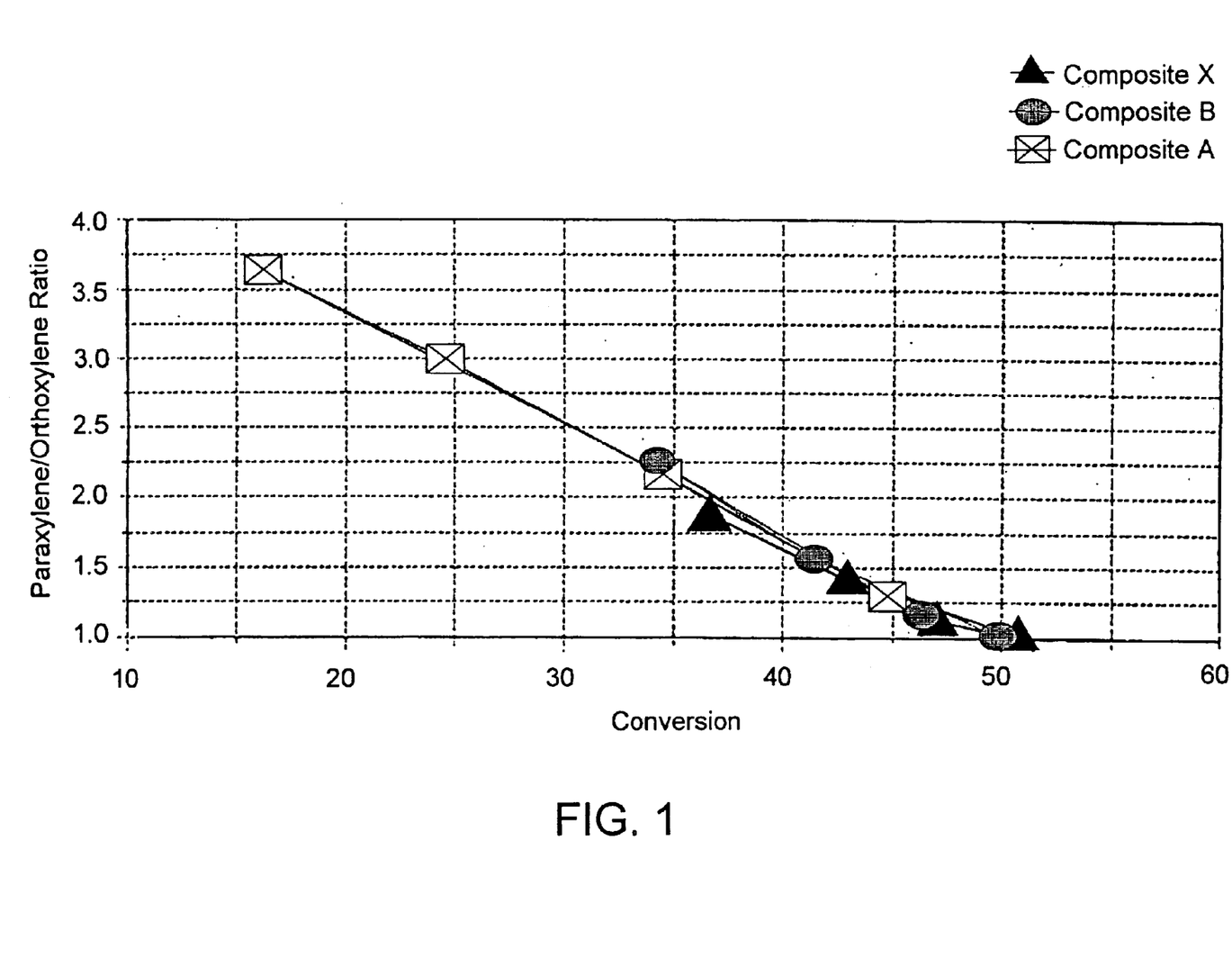
FIG. 1 shows selectivity as paraxylene/orthoxylene ratio vs. conversion in a microreactor test of toluene disproportionation for composites; of the invention and a control catalyst.

FIG. 1 shows the results of the micro-reactor tests. Composites A and B demonstrated the most favorable ratio of paraxylene to orthoxylene, with Composite A achieving nearly a 4:1 para-/ortho-ratio at low conversions.

Example IV

Comparative disproportionation selectivity was investigated further by testing isomerization of xylenes for a composite of the invention relative to a composite of the art; through reversion of paraxylene to equilibrium xylenes, isomerization would impact selectivity unfavorably.

Figure 2:
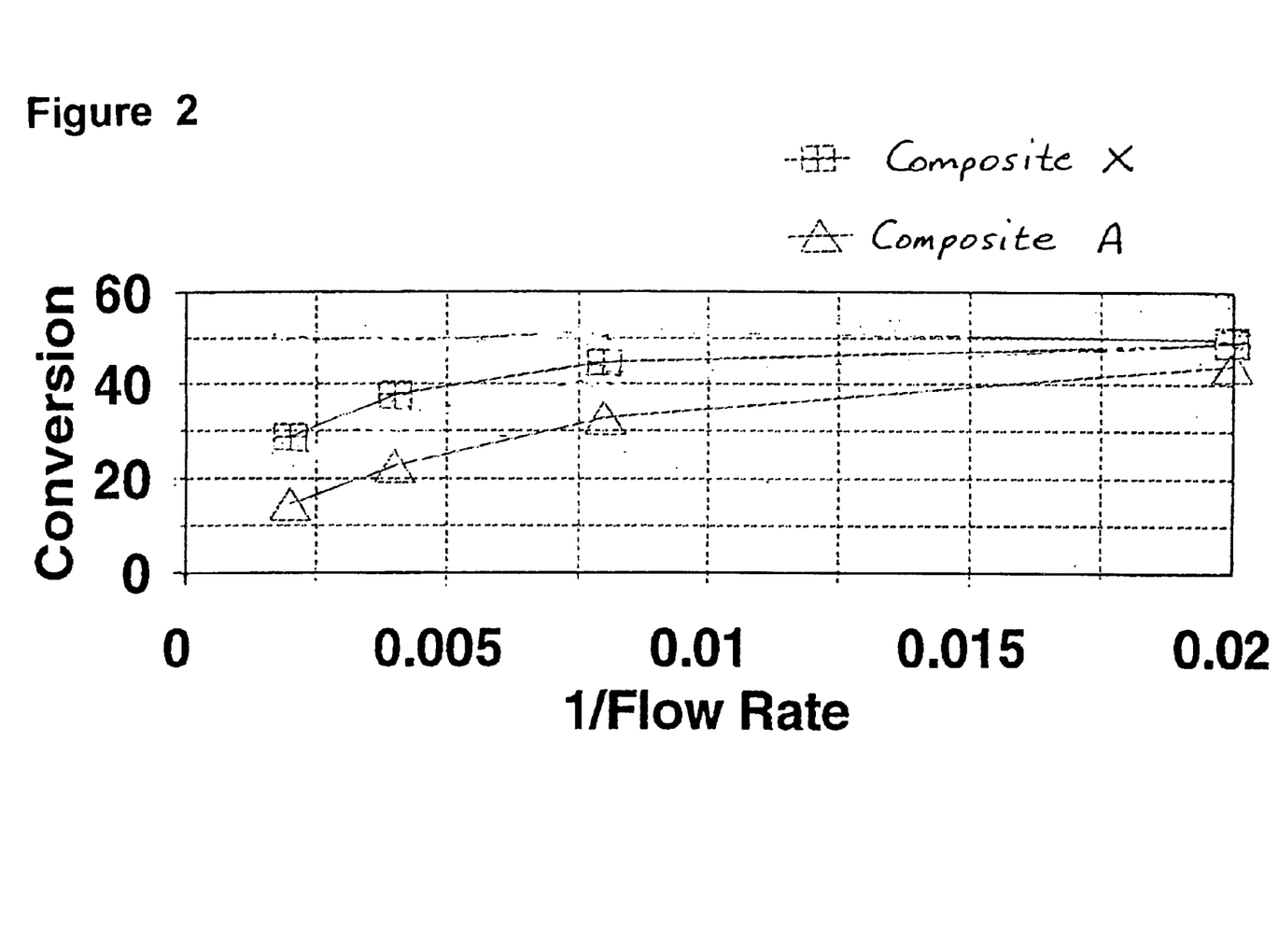
FIG. 2 shows disproportionation conversion vs. the inverse of flow rate for a composite of the invention and a control catalyst, indicating potential product re-isomerization.

Composites A and X therefore were tested for isomerization activity, using a metaxylene feedstock. The results are plotted in FIG. 2, showing conversion vs. the inverse of the flow rate. Composite A demonstrated much less potential for reversion of xylene isomers via isomerization, and therefore greater potential as a catalyst for high disproportionation selectivity.

Example V

Figure 3:
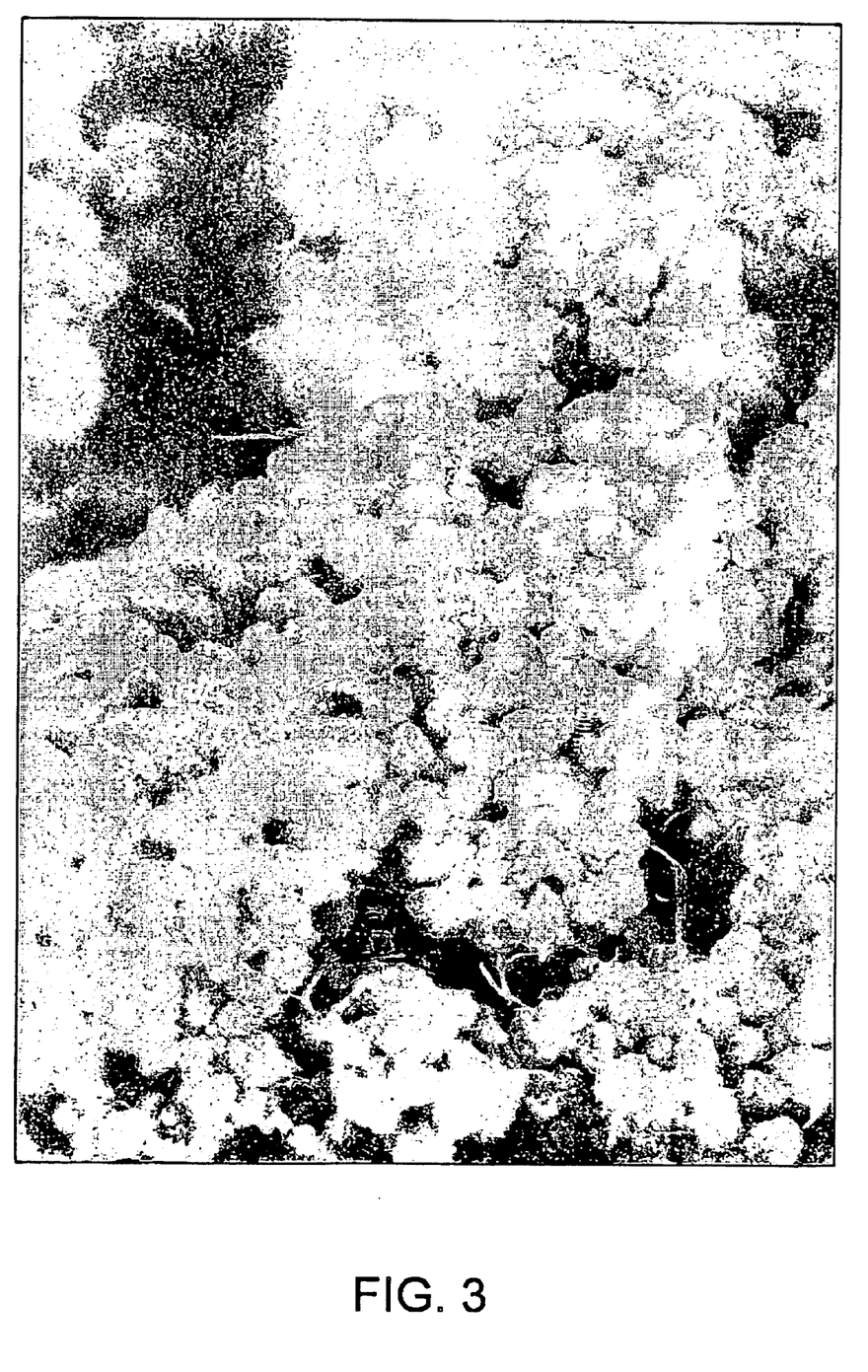
FIG. 3 shows an SEM micrograph of a composite of the known art.
Figure 4:
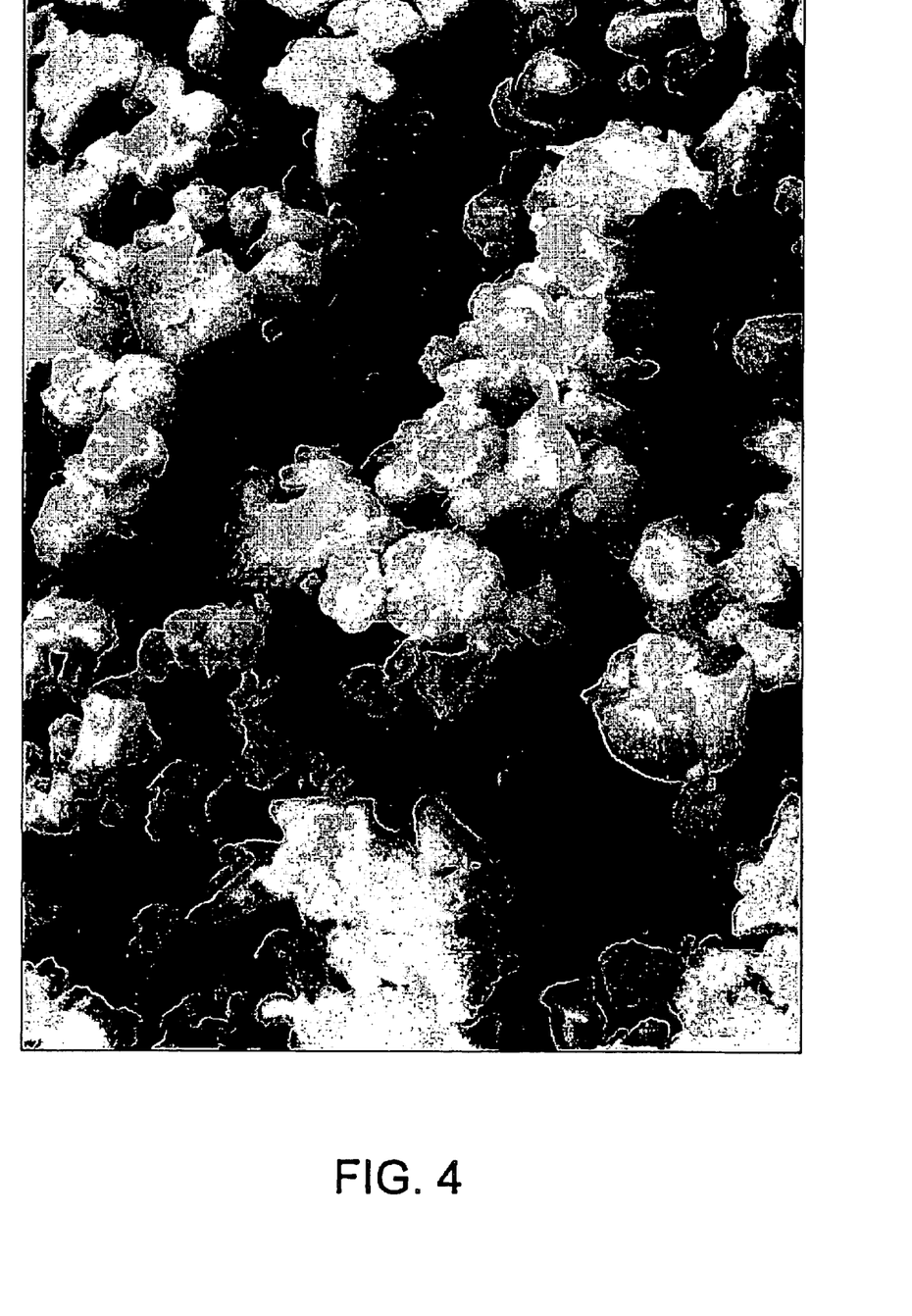
FIG. 4 shows an SEM micrograph of a composite of the invention.

Composites A and X were examined by Scanning Electron Microscope (SEM), using a Leica Stereoscan 420 at an accelerating voltage of 10 kV. Comparative SEM micrographs at magnifications of 10,000×are shown respectively in FIGS. 3 and 4. The micrograph of Composite A of the invention shows crystals having substantial planar surfaces, with many crystals of a size well in excess of 1 $\mu$m. The micrograph of Composite X of the art shows agglomerations of crystals having relatively irregular faces, with most crystals of a size of about 1 $\mu$m or less.

We claim:

1. A layered crystalline metallosilicate composite wherein layers are contiguous, compositionally heterogeneous and of a single zeolitic isotype and comprise:
   (a) a catalytically active core comprising a zeolitic aluminosilicate selected from the group consisting of MFI, MEL, MTW and TON having a $SiO_2$:$Al_2O_3$ ratio below 45; and,
   (b) a mantle comprising a crystalline metallosilicate consisting essentially of boralite which comprises a framework metal consisting essentially of boron.

2. The composite of claim 1 wherein the crystalline metallosilicate of (b) is characterized by an empirical chemical composition of an anhydrous basis expressed by the formula:

0.9±0.2 $X_{2/n}$O:$B_2O_3$:$y$$SiO_2$ where X is a cation of valence n and y is between about 4 and 500.

3. The composite of claim 1 wherein the crystalline metallosilicate composite consists essentially of:
   (a) a catalytically active core comprising a zeolitic aluminosilicate, and,
   (b) a mantle comprising a crystalline boralite.

4. The composite of claim 1 further comprising an aluminum phosphate binder.

5. A process for the disproportionation of a toluene-containing feedstock comprising contacting the feedstock with a layered crystalline metallosilicate composite wherein layers are contiguous, compositionally heterogeneous and of an MFI isotype and comprise:
   (a) a catalytically active core comprising a zeolitic aluminosilicate, having a $SiO_2$:$Al_2O_3$ ratio less than about 45 and,
   (b) a mantle comprising a crystalline boralite;
in a disproportionation zone at disproportionation conditions to obtain a paraxylene-rich product.

6. The process of claim 5 wherein the disproportionation conditions comprise a temperature of from about 200° to 600° C., a pressure of from about 100 kPa to 6 MPa absolute, and a liquid hourly space velocity of from about 0.2 to 10 $hr^{-1}$.

7. The process of claim 6 wherein free hydrogen is present in a molar ratio to feedstock hydrocarbons of about 0.5 to 10.

8. The process of claim 5 wherein the composite consists essentially of a catalytically active core comprising a zeolitic aluminosilicate having a $SiO_2$:$Al_2O_3$ ratio between about 20–40, a mantle comprising a crystalline boralite, and an aluminum phosphate binder.

9. The process of claim 5 wherein the product contains paraxylene in excess of its equilibrium concentration at disproportionation conditions.

10. The process of claim 5 further comprising deposition at precoking conditions of between about 5 and 40 mass-% carbon on the composite prior to its use for disproportionation of the feedstock.

11. The process of claim 10 wherein the precoking conditions comprise a temperature at least about 90° C. higher than utilized in the subsequent disproportionation.

* * * * *